(12) United States Patent
Guglielmi et al.

(10) Patent No.: US 8,642,049 B2
(45) Date of Patent: Feb. 4, 2014

(54) VACCINE AGAINST GROUP A BETA HEMOLYTIC STREPTOCOCCUS AND RESPECTIVE PROCESS FOR OBTAINING THEREOF

(76) Inventors: Luiza Guilherme Guglielmi, Sao Paulo (BR); Jorge Elias Kalil Filho, Sao Paulo (BR)

( * ) Notice: Subject to any disclaimer, the term of this patent is extended or adjusted under 35 U.S.C. 154(b) by 687 days.

(21) Appl. No.: 12/516,754

(22) PCT Filed: Jul. 19, 2007

(86) PCT No.: PCT/BR2007/000184
§ 371 (c)(1),
(2), (4) Date: Jan. 19, 2010

(87) PCT Pub. No.: WO2008/064440
PCT Pub. Date: Jun. 5, 2008

(65) Prior Publication Data
US 2010/0183518 A1    Jul. 22, 2010

(30) Foreign Application Priority Data

Nov. 30, 2006   (BR) ...................................... 0604997

(51) Int. Cl.
*A61K 39/09*   (2006.01)
(52) U.S. Cl.
USPC ........................................ 424/244.1; 530/350
(58) Field of Classification Search
None
See application file for complete search history.

(56) References Cited

U.S. PATENT DOCUMENTS

| | | | |
|---|---|---|---|
| 6,063,386 A * | 5/2000 | Dale et al. .................. | 424/244.1 |
| 6,358,704 B1 | 3/2002 | Holmes et al. | |
| 6,602,507 B1 | 8/2003 | Fischetti | |
| 6,716,433 B1 * | 4/2004 | Dale .......................... | 424/244.1 |
| 2002/0176863 A1 | 11/2002 | Dale | |
| 2005/0002956 A1 | 1/2005 | Lowell et al. | |

FOREIGN PATENT DOCUMENTS

| | | |
|---|---|---|
| BR | PI 0501290-2 | 3/2005 |
| WO | 89/09064 | 10/1989 |
| WO | 90/15872 | 12/1990 |
| WO | 94/06465 | 3/1994 |
| WO | 2004/014956 | 2/2004 |

OTHER PUBLICATIONS

Greenspan et al (Nature Biotechnology 7: 936-937, 1999).*
Chothia et al (The EMBO Journal, 1986, 5/4:823-26).*
Abbas et al. Cellular and Molecular Immunology 4th edition chapter 15 p. 360-362, 2000.*
Ellis, R.W. (Chapter 29, pp. 568-575, of "Vaccines" [Plotkin, S.A. et al. (eds) published by W. B. Saunders company (Philadelphia) in 1988.*
Official Action dated Nov. 8, 2012 for Japanese Application No. 2009538555 and translation.
Guilherme, et. al., Towards a vaccine against rheumatic fever, Clinical & Developmental Immunology, Jun.-Dec. 2006; 13(2-4): 125-132.
Supplementary European Search Report for EP Application No. 07784913.1 dated Nov. 30, 2012.
Official Action dated Jul. 23, 2013 for EP 07784913.1.

* cited by examiner

*Primary Examiner* — Jennifer Graser
(74) *Attorney, Agent, or Firm* — Ladas & Parry LLP

(57) ABSTRACT

VACCIN AGAINST GROUP A BETA HEMOLYTIC STREPTOCOCCUS AND RESPECTIVE PROCESS FOR OBTAINING THEREOF, which predicts the production of recombinant protein cloned from the gene emm5, which contains a sequence of oligonucleotides corresponding to 52 and/or 87 amino acid residues capable of protection, isolated after the sequential molecular identification of the epitopes from the M protein carboxy-terminal region, differing in 01 amino acid residue, identified by antibodies and T lymphocytes of health human beings and of patients carriers of rheumatic fever, capable of generating a protective response by antibodies depending on the T lymphocytes; prevention of the development of the autoimmune disease by the selected epitope was evaluated in vitro with T lymphocytes from the cardiac tissue of patients with lesions arising out of rheumatic fever.

1 Claim, 1 Drawing Sheet

FIG. 1

Lys-Gly-Leu-Arg-Arg-Asp-Leu-Asp-Ala-Ser-Glu-Arg-Ala-Lys-
Lys-Gln-Leu-Glu-Ala-Glu-Gln-Lys-Leu-Glu-Gln-Asn-
Lys-Ile-Ser-Glu-Ala-Ser-Arg-Lys-Gly-Leu-Arg-Arg-Asp-Leu-
Asp-Ala-Ser-Arg-Glu-Ala-Lys-Lys-Gln-Val

FIG. 2

Lys-Gly-Leu-Arg-Arg-Asp-Leu-Asp-Ala-Ser-Glu-Arg-Ala-Lys-
Lys-Gln-Leu-Glu-Ala-Glu-His-Gln-Lys-Leu-Glu-Gln-Asn-
Lys-Ile-Ser-Glu-Ala-Ser-Arg-Lys-Gly-Leu-Arg-Arg-Asp-Leu-
Asp-Ala-Ser-Glu-Arg-Ala-Lys-Lys-Gln-Leu-Ala-Glu-Gln-
Gln-Lys-Leu-Glu-Gln-Gln-Asn-Lys-Ile-Ser-Glu-Ala-Ser-Arg-
Lys-Gly-Leu-Arg-Arg-Asp-Leu-Asp-Ala-Ser-Arg-Glu-Ala-Lys-
Lys-Gln-Val

SEQUENCE LISTING

<160> NUMBER OF SEQ ID NOS: 2

<210> SEQ ID NO 1
<211> LENGTH: 52
<212> TYPE: PRT
<213> ORGANISM: ARTIFICIAL SEQUENCE
<220> FEATURE:
<223> OTHER INFORMATION: SYNTHETIC

<400> SEQUENCE: 1

Lys Gly Leu Arg Arg Asp Leu Asp Ala Ser Glu Arg Ala Lys Lys Gln
1               5                   10                  15

Leu Glu Ala Glu Gln Gln Lys Leu Glu Glu Gln Asn Lys Ile Ser Glu
            20                  25                  30

Ala Ser Arg Lys Gly Leu Arg Arg Asp Leu Asp Ala Ser Arg Glu Ala
        35                  40                  45

Lys Lys Gln Val
    50

<210> SEQ ID NO 2
<211> LENGTH: 87
<212> TYPE: PRT
<213> ORGANISM: ARTIFICIAL SEQUENCE
<220> FEATURE:
<223> OTHER INFORMATION: SYNTHETIC

<400> SEQUENCE: 2

Lys Gly Leu Arg Arg Asp Leu Asp Ala Ser Glu Arg Ala Lys Lys Gln
1               5                   10                  15

Leu Glu Ala Glu His Gln Lys Leu Glu Glu Gln Asn Lys Ile Ser Glu
            20                  25                  30

Ala Ser Arg Lys Gly Leu Arg Arg Asp Leu Asp Ala Ser Glu Arg Ala
        35                  40                  45

Lys Lys Gln Leu Glu Ala Glu Gln Gln Lys Leu Glu Glu Gln Asn Lys
    50                  55                  60

Ile Ser Glu Ala Ser Arg Lys Gly Leu Arg Arg Asp Leu Asp Ala Ser
65                  70                  75                  80

Arg Glu Ala Lys Lys Gln Val
                85

VACCINE AGAINST GROUP A BETA HEMOLYTIC STREPTOCOCCUS AND RESPECTIVE PROCESS FOR OBTAINING THEREOF

FIELD OF THE INVENTION

The Applicant already holds patent application PI 0501290-2, filed on Mar. 24, 2005, referring to a "VACCINE AGAINST GROUP A BETA HEMOLYTIC STREPTOCOCCUS AND RESPECTIVE PROCESS FOR OBTAINING THEREOF". This patent refers to a new vaccine whose purpose is the same, as well as a new process to obtain the new vaccine.

BACKGROUND OF THE INVENTION

In the previous patent application PI 0501290-2, the state of the art with respect to vaccines against streptococci of the beta hemolytic group A type was duly described. This state of the art will be described again here, since this invention refers to the same subject.

As it is known in the art, rheumatic fever (RF) is a disease caused by infection by the group A beta hemolytic *streptococcus*, or *S. pyogenes*, a disease that is manifested in children between age 3 and 18, who present genetic susceptibility factors and who were not treated. The illness is initially manifested in the clinical form of polyarthritis (pains in the large articulations), followed by a clinical condition that involves two main manifestations: Sydenham's chorea and rheumatic carditis.

The chorea manifests in about 20-30% of patients with rheumatic fever (RF); the affected organ is the central nervous system (CNS) and the manifestations are translated into involuntary movements, psychiatric disorders, which disappear with adequate treatment.

Rheumatic carditis manifests in about 30-45% of patients with rheumatic fever (RF); it is characterized by an acute heart inflammation, initially in the myocardium, and produce serious, progressive and permanent lesions in the valve tissue, affecting mainly the mitral and aortic valves and triggering chronic rheumatic heart disease (RHD). The treatment of RHD in more advanced stages is surgical. Considering the age range of manifestation of the disease, children between age of 7 and 12, they frequently have to be operated for correction of valve lesions or to substitute the valves by biological prostheses (Snitcowski, 1996).

In Brazil, 90% of child cardiac surgeries result from rheumatic valve lesions. The cardiac surgeries in adult rheumatic individuals correspond to 30% of this total (Data from the Ministry of Health, DATA-SUS).

Epidemiology:

Rheumatic fever (RF) and chronic rheumatic heart disease (RHD) are still considered as a public health problem in developing and underdeveloped countries. It is estimated that there are more than 50 million cases of rheumatic fever (RF) in the world, and, according to recent data from the World Health Organization (WHO), there are records of 14 million cases of chronic rheumatic heart disease (RHD) in the world. The prevalence of RHD is higher than 10 children in each 1000 with RF in various countries, among them: Iran, Thailand, China, Bolivia, Pakistan, India, Australia, Argelia, Egypt and Morocco. Brazil has an average of 6.5 children with RHD per 1000 RF carriers. Moreover, more than 18 million cases of streptococci per year and more than 500000 deaths per year by streptococci are recorded at the WHO (2004).

Pathogenesis of the Disease:

Rheumatic fever (RF) is considered an autoimmune disease resulting from the defense immune response triggered against the group A beta hemolytic *streptococcus*, or *S. pyogenes*, and that, in some individuals (those with susceptibility to the illness), produces an aggressive response against the organism's own proteins through biological mimicry mechanisms.

It is currently known that antibodies and the immune response mediated by T-Cell lymphocytes are responsible for the cross reactions against proteins of the human tissue (heart, articulations, kidney, brain) (revised by Cunningham, 2000; Guilherme et al, 1995). These cross-reactions occur due to the similarity in the structure or residues of amino acids, especially with protein M of the *streptococcus*.

The M-protein sequences were analyzed and published in the 1980s (Manjula e Philipis, 1984, and Miller et al, 1998), and permitted great advance in the knowledge of the regions capable of triggering the illness, through a number of scientific works published by several groups.

The M-protein contains regions of repetitions of amino acid residues, and is subdivided into an amino-terminal portion and a carboxy-terminal portion. In the amino-terminal portion are located the residues of amino acids that define the *streptococcus* serotype. The carboxy-terminal portion is quite conserved among the different serotypes and has groups of amino acids groups that repeat themselves more than once (Fischetti, 1991).

Several segments of the amino-terminal region are described because they are involved in the triggering of the disease (rheumatic fever and/or chronic rheumatic heart disease), especially through cross-reaction with proteins of the cardiac tissue (revised by Cunningham, 2000 and Guilherme et al, 2005).

It is interesting to note that until the 80s, it was believed that cross-reactions between the *streptococcus* and the proteins of the human tissue resulted only from an antibody-mediated immune response. From the description of the presence of inflammatory infiltrates in the cardiac tissue with predominance of $CD4^+$ T lymphocyte (Raizada et al, 1983, and Kemeny et al, 1989), the Applicant demonstrated that the heart lesions were mediated by these cells ($CD4^+$ T lymphocytes). This evidence was defined by the detection of the immune response of the cross reaction between proteins isolated from fragments of human cardiac tissue (myocardium and valvular), by infiltrating T lymphocytes of the heart lesion in patients that carried RHD, obtained through a surgical act, to correct the valve lesions (Guilherme et al, 1995). Subsequently, the Applicant described the presence of great number of mononuclear cells that produced particularly inflammatory cytokines (interferon gama, IFNg; and tumor necrosis factor alpha, TNFa) in the cardiac tissue (myocardium and mitral and/or aortic valves) of patients suffering from rheumatic heart disease. The relevant finding of this work was the observation of the presence of great number of cytokine producing cells, which regulate the inflammation (interleukines 10 and 4, IL-10 and IL-4) in the myocardium and rare cells producing the IL-4 regulatory cytokine, in the valve tissue. This finding showed why post-streptococcal myocarditis heals in approximately 4 weeks and the lesions of the mitral and/or aortic valves are slow, progressive and permanent (Guilherme et al, 2004).

Considering that rheumatic fever is an autoimmune disease, understanding the pathogenesis of rheumatic fever is fundamental to its prevention, because it leads to care being taken to produce a vaccine against the cause agent, the group A beta hemolytic *streptococcus* (*S. pyogenes*), in the sense of not triggering the autoimmune disease.

There already are several vaccines against group A beta hemolytic *streptococcus*.

Prof. James B. Dale (University of Tennessee Research Foundation) is carrying out research to produce a vaccine based on the sequences of the amino-terminal residues of protein M, which confer the *streptococcus* specificity. He has several published works (Beachey et al, 1987; Dale et al, 1993; Dale et Chang, 1995; Dale et al, 1999, a, b and c); and he has already analyzed the response capacity in 26 different serotype animal models. There are several patents filed in his behalf, among which U.S. Pat. No. 6,716,433, filed on Sep. 10, 1998 and granted on Apr. 6, 2004 ("GROUP A STREPTOCOCCAL VACCINES").

Recently, the group published a "phase I" work, using vaccine formulation containing 06 different serotypes in the form of a recombinant protein containing N-terminal segments of the 06 serotypes. Cross-reaction control was conducted on human tissue slices and only the humoral response (antibody mediated) was evaluated (Kotloff, 2004). The multivalent vaccine produced to prevent streptococcal infection against 26 serotypes of *S. pyogenes*, is undergoing phase II clinical tests (McNeil et al, 2005).

Prof. Vincent Fischetti (The Rockefeller University) is conducting research for the production of a vaccine based on the sequences of the carboxy-terminal residues of protein M, which confer *streptococcus* specificity. By cloning the gene that codifies protein M6 (portions N and C-terminal) the group found that 56 different streptococci serotypes presented the homology of the amino acids sequence in the carboxy-terminal region (Scott et al, 1985 e 1986). Through intranasal inoculation of peptides of the carboxy-terminal region of protein M6 in rabbits, Prof. Fischetti's group showed the possibility of altering the group A *streptococcus* bacterial colonization (Bessen et Fischetti, 1988, a and b). Using vaccines with synthetic peptides with shared sequences covalently linked and conjugated with the sub-unit of the CTB cholera toxin, they induced the formation of IgA type antibodies specific for protein M with a protective activity in the serum and in the saliva of mice (Bessen et Fischetti, 1990, and Fluckiger et al, 1998).

In subsequent works, these authors used the vaccinia virus as a vector, containing the total sequence of the C-terminal portion of protein M6, to produce the recombinant vaccine—VV: M6-, showing that a single intranasal dose was capable of preventing the heterologous streptococci bacterial colonization. Intradermal immunization was ineffective (Fischetti et al, 1985). The high cost of conjugation and the intranasal use of the vaccinia virus, in the models cited above limited the use of these models as a safe, effectively and financially accessible vaccine. Tests with commensal bacteria as vectors were also used (Fischetti et al, 1993; Medaglini et al, 1995). The use of this commensal vector as a vehicle of the vaccine is under analysis. Preliminary results have suggested that the vector was safe and well tolerated, when administered orally or nasally, in 150 healthy voluntaries (Kotloff et al, 2005).

There are some patents filed in his name, among them, U.S. Pat. No. 6,602,507, filed on Jan. 6, 1995 and granted on Jan. 5, 2003 ("SYNTHETIC PEPTIDES FROM STREPTOCOCCAL M PROTEIN AND VACCINES PREPARED THEREFROM"). The formulation of vaccine of the C-terminal portion expresses how fusion protein on the surface of *Streptococcus* gordoni, is currently undergoing clinical phase I tests (WHO, 2006).

Prof. M. Good has been approaching the use of peptides from the C-terminal portion as a possible vaccine model in Australia, where the incidence of streprotococcal infections in the aborigine populations, and consequently of rheumatic fever is high. Australian researchers identified a peptide composed by 09 amino acid residues of the C-terminal portion, capable of producing opsonizing antibodies in immunized mice. This antibody was also present in the serum of normal individuals and patients with rheumatic disease (Pruksakorn et al, 1994, and Brandt et al, 1997). Recently, the group has been working with a combination of segments from the amino-terminal portions of some serotypes prevailing in Australia and the segment of the carboxy-terminal portion, referred to as J14 (Dunn et al, 2002; Olive et al, 2002). The group's most recent results show that segment J14 (29 amino acid residues) favor the development of protective antibodies, capable of inducing fagocytosis in an experimental model of mouse, against various strains of *S. pyogenes* from isolated points from the endemic regions of Australia. The in vivo challenge of these animals confirmed the protective capacity of peptide J14 in several formulations (Vohra et al, 2005; Batzloff et al, 2005; Olive et al, 2005).

SUMMARY AND OBJECTS OF THE INVENTION

The object of this patent of Invention refers to a new vaccine against the group A beta hemolytic *streptococcus*, as well as new process to obtain said new vaccine, the latter providing two formulations, and the process providing for a modification in relation to the procurement process contemplated by Applicant in its previous patent application PI 0501290-2.

BRIEF DESCRIPTION OF THE DRAWINGS

A more complete appreciation of the present invention and many of the attendant advantages thereof will be readily understood by reference of the following detailed description when taken in conjunction with the accompanying drawings, in which:

FIG. 1 attached illustrates the sequence of residues selected in a first model (first formulation) (SEQ ID NO:1).

FIG. 2 attached illustrates the sequence of the residues selected in a second model (second formulation) (SEQ ID NO:2).

DETAILED DESCRIPTION OF THE INVENTION

The object of this patent of Invention refers to a new "VACCINE AGAINST THE GROUP A BETA HEMOLYTIC STREPTOCOCCUS", as well as new "PROCESS TO OBTAIN" said new vaccine, the latter providing two formulations, and the process providing for a modification in relation to the procurement process contemplated by Applicant in its previous patent application PI 0501290-2.

In short, the sequence of epitope B was identified by the analysis of 79 synthethic peptides differing in 01 amino acid residue, per serums of 620 individuals (health human beings and carriers of rheumatic fever). Epitope T, in turn, was identified using mononuclear cells of the peripheral blood of 258 individuals (health human beings and carriers of rheumatic fever), and tested against 38 synthetic peptides of M protein carboxy-terminal portion, selected from the 79 peptides tested for definition of epitope B (Guilherme et al, 2006; Patent Application PI 0501290-2).

According to this patent, the construction of two vaccine models was contemplated, in the form of synthetic peptides and/or recombinant proteins, containing:

1. The T and B epitopes of the carboxy-terminal region of protein M composed by 156 pb (corresponding to 52 residues of amino acids), which contemplates the following sequences of amino acids: 22 residues corresponding to epitope T, followed by 8 intermediary residues and 22 residues of epitope B; and
2. Epitopes T and B of the carboxy-terminal region of protein M composed by 261 pb (corresponding to 87 residues of amino acids), which contemplates the following sequences of amino acids: 22 residues corresponding to epitope T, followed by 8 intermediary residues, 27 residues of a hybrid T-B epitope and 22 epitope B residues.

In the first model, the vaccine as synthetic peptides and/or recombinant proteins contains segments of 52 amino acid residues from the carboxy-terminal region of protein M (epitope T, 08 intermediary residues and epitope B).

FIG. 1 attached illustrates the sequence of residues selected in this model.

In the second model, the vaccine as synthetic peptides and/or recombinant proteins contains segments of 87 amino acid residues of the carboxy-terminal region of protein M (epitope T, 08 intermediary residues, hybrid T-B, 08 intermediary residues and epitope B).

FIG. 2 attached illustrates the sequence of the residues selected in this model.

These residues from amino acids of the carboxy-terminal region of the M protein are capable of generating a response mediated by antibodies and T $CD4^+$ lymphocytes, protective and that does not trigger an autoimmune disease.

These sequences differ from those previously used for the preparation of vaccines, as exposed below:

James B. Dale uses the amino-terminal region of various serotypes (U.S. Pat. No. 6,716,433).

Vincent A. Fischetti uses the carboxy-terminal region of protein M6 (U.S. Pat. No. 6,602,507). Consists of 06 groups of polypeptides. Group 04 presents its identity with 19 amino acid residues components of the segment that contains epitopes T and B (Guilherme et al, 2006) selected by Applicant.

M. Good uses the carboxy-terminal region associated with amino-terminal of strains prevailing in Australian Aborigines. He shows identity with 18 residues of amino acids components of the segment that contains epitopes T and B (Guilherme et al, 2006) selected by Applicant, of which 14 residues are common to the components of group 04 of protein M6, identified by V. A. Fischetti.

Below are described the stages of the new process for obtaining the now innovated vaccine:
Stage 1: Cloning of the regions of 52 and 87 amino acid residues to produce recombinant proteins, from gene emm5;
Stage 2: Tests in laboratory animals, preferably mice;
Stage 3: Safety tests: tests in animals, and continuity of in vitro tests for prevention of autoimmunity (cell proliferation tests and determination of cytokines) by the vaccine epitopes using the lineage of T-Cell intralesion lymphocyte, from surgical fragments of the cardiac tissue of cardiac rheumatic disease carriers.

The vaccine innovated now is different from existing ones, bringing advantages in relation to the models proposes, as commented below:

The selection of protective epitopes was performed based on published sequences of the changing M5 protein (Robinson et al, 1991), used for preparation of synthetic peptides for evaluation of epitopes with pathogenic potential (N-terminal region) (Guilherme et al 1995 and 2001) and epitopes from the C-terminal region, able to protect against the disease, evaluated by in vitro tests with a large number of samples (serums of 620 individuals and T-Cell lymphocytes from 258 individuals) (Guilherme et al, 2006).

Scanning of the carboxy-terminal region (residues of 240 to 350) was performed using 79 synthetic peptides with 20 amino acid residues with difference of only 01 (one) amino acid residue. This approach is unique and permitted molecular definition of the regions with protective capacity (Guilherme et al, 2006; Patent Application PI 0501290-2).

Cross-reaction tests were performed, analyzed from a collection of lineages from 20 infiltrating lymphocytes of the cardiac tissue of patients with RHD, obtained during the surgical procedure performed to correct valve lesions, and expanded in vitro, as previously described (Guilherme et al, 1995).

The production of recombinant protein is based on strain M5, since the studies conducted with synthetic peptides were based on a published sequence of this protein (Robinson et al, 1991).

REFERENCES

US Patent Documents

U.S. Pat. No. 6,602,507, filed on Jan. 6, 1995 and granted on Aug. 5, 2003;
U.S. Pat. No. 6,716,433, filed on Sep. 10, 1998 and granted on Apr. 6, 2004;
U.S. Pat. No. 6,358,704, filed on Jan. 28, 1999, granted on Mar. 19, 2002.

OTHER REFERENCES

1. Beachey E H, Seyer J M, Dale J B: "Protective immunogenecity and T lymphocyte specificity of a trivalent hybrid peptide containing NH2-terminal sequences of types 5, 6 and 24 M proteins synthesized in tandem". J. Exp. Med. 1987; 166:647-656.
2. Bessen D, Fischetti V A: "Influence of intranasal immunization with synthetic peptides corresponding to conserved epitopes of M protein on mucosal colonization by group A streptococci". Infect. Immun. 1988; 565: 2666-2672.
3. Bessen D, Fischetti V A: "Passive acquired mucosal immunity to group A streptococci by secretory immunoglobulin". A. J. Exp. Med. 1988; 167: 1945-1949.
4. Bessen D, Fischetti V A: "Synthetic peptide vaccine against mucosal colonization by group A streptococci. I. protection against a heterologous M serotype with shared C repeated region epitopes". J. Immunol. 1990; 145 (4): 1251-12.
5. Brandt E R, Hayman W A, Currie B, Pruksakorn S, Good M F: "Human antibodies to the conserved region of the M protein: opsonization of heterologous strains of group A streptococci". Vaccine 1997; 15: 1805-1812.
6. Cunningham, M. W. (2000): "Pathogenesis of group A streptococcal infections". Clin. Microbiol. Rev. 470-511.
7. Dale J B, Chang E C: "Intranasal immunization with recombinant group A streptococcal M fragment fused to the B subunit of *Eschirichia coli* labile toxin protects mice against systemic challenge infections". J. Infect. Dis, 1995; 171: 1038-1041.
8. Dale J B, Chang E Y, Lederer J W. "Recombinant tetravalent group A streptococcal M protein vaccine". J. Immunol. 1993, 151 (4): 2188-2194.

9. Dale J B, Simmons M, Chiang E C, Chiang E Y: "Recombinant, octavalent group A streptococcal M protein vaccine". Vaccine. 1999, 14 (10): 944-948.
10. Dale, J B: "Multivalent group A streptococcal vaccine designed to optimize the immunogenecity of six tandem M protein fragments". Vaccine, 1999. 17:193-200.
11. Dale, J B, Chiang E Y., Liu S., Courtney H S., Hasty, D L. "New protective antigen of group A streptococci". J. Clin. Invest. 1999. 103:1261-1268.
12. Dunn, L A, McMillan D J, Batzloff M, Zeng W, Jackson D C J, Uperoft J A, Uperoft P, Olive C: "Parenteral and mucosal delivery of a novel multi-epitope M protein-based group A streptococcal vaccine construct: investigation of immunogenecity in mice". Vaccine, 2002, 20: 2635-2640.
13. Fischetti V A, Jones K F, Scott J R.: "Size variation of the M protein in group A streptococci". J. Exp. Med. 1985, 161: 1384-1401.
14. Fischetti V A, Medaglini D, Oggioni M, Pozzi G: "Expression of foreign proteins on gram—positive commensal bacteria for mucosal delivery". Curr. Opin Biotech. 1993, 4:503-610.
15. Fischetti, V.: "Streptococcal M protein". Sci. Am.:1991 264(6): 32-39.
16. Fluckiger, U.; Jones K F; Fischetti, V A: "Immunoglobulins to group A streptococcal surface molecules decrease adherence to and invasion of human pharyngeal cells". Infect. Immun. 1998. 66: 974-979.
17. Guilherme L, Cunha-Neto E, Coelho V, Snitcowsky R, Pomerantzeff P. M A, Assis R V, Pedra F, Neumann J, Goldberg A, Patarroyo M E, Pillegi F, Kalil J: "Human-infiltrating T cell clones from rheumatic heart disease patients recognize both streptococcal and cardiac proteins". Circulation 1995; 92: 415-420.
18. Guilherme, L., Oshiro, S. E., Faé, K. C., Cunha-Neto, E., Renesto, G et al: "T cell reactivity against streptococcal antigens in the periphery mirrors reactivity of heart infiltrating T lymphocytes in rheumatic heart disease patients". Infect. Immun, 2001, 69: 5345-5351.
19. Guilherme L., P. Cury, L. M. Demarchi, V. Coelho, L. Abel, A. P. Lopez, S. E. Oshiro, S. Aliotti, E. Cunha-Neto, P. M. Pomerantzeff, A. C. Tanaka and J. Kalil: Rheumatic heart disease: proinflammatory cytokines play a role in the progression and maintenance of valvular lesions. Am J Pathol, 2004, 165:1583-91.
20. Guilherme, L Faé, K C, Oshiro, S E, Kalil, J: Molecular pathogenesis of Rheumatic fever and rheumatic heart disease. Exp. Rev Mol Méd, 2005, 7(28): 1-15.
21. Guilherme, L Faé, K C, Higa F, Chaves, L, Oshiro, S E, Freschi de Barros, S, Puschel, C, Juliano, M A, Tanaka, A C, Spina, G, Kalil, J: Towards a vaccine against rheumatic fever. Clin Dev Immunol, 2006,XX 1-8.
22. Kemeny, E., Grieve, T., Marcus, R., Sareli, P., Zabriskie, J B: "Identification of mononuclear cells and T cell subsets in rheumatic valvulitis". Clin. Immunol. Immunopathol. 1989, 52:225-237.
23. Kotloff K, Correti M, Palmer K, Campbell J D, Reddish M A, Hu M C, Wasserman S S, Dale J B: "Safety and immunogenecity of a recombinant multivalent group A streptococcal vaccine in healthy adults". J. Am. Med. Assoc (JAMA), 2004, 11: 709-715.
24. Kotloff K L, Wasserman S S, Jones K F, Livio S, Hruby D E, Franke C A, Fischetti V A: Clinical and microbiological responses of volunteers to combined intranasal and oral inoculation with a *Streptococcus gordonii* carrier strain intended for future use as a group A *streptococcus* vaccine. Infect Immun, 2005, 73(4):2360-6.
25. Manjula, B. N., Acharya, A. S., Mische, M. S., Fairwell, T. and Fischetti, V. A.: "The complete amino acid sequence of a biologically active 197—residue fragment of M protein isolated from type 5 group A streptococci". J. Biol. Chem., 1984, 259, 3686-3693.
26. Medaglini D, Pozzi G, King T P, Fischetti V A: "Mucosal and systemic immune response to a recombinant protein expressed on the surface of the oral commensal bacterium *Streptococcus gordoni* after oral colonization". Proc. Natl. Acad. Sci. USA, 1995, 92: 6868-6872.
27. McNeil S A, Halperin S A, Langley J M, Smith B, Warren A, Sharratt G P, Baxendale D M, Reddish M A, Hu M C, Stroop S D, Linden J, Fries L F, Vink P E, Dale J B.: Safety and immunogenicity of 26-valent group a *streptococcus* vaccine in healthy adult volunteers. Clin Infect Dis, 2005, 41(8):1114-22.
28. Miller, L. C., Gray, E. D., Beachey, E. H. and Kehoe, M. A.: "Antigenic variation among group A streptococcal M proteins: nucleotide sequence of the serotype 5 M protein gene and its relationship with genes encoding types 6 and 24 M proteins". J. Biol. Chem., 1988, 263, 5668-5673.
29. Olive C, Clair T, Yarwood P, Good M: "Protection of mice from group A streptococcal infection by intranasal immunisation with a peptide vaccine that contains a conserved M protein B cell epitope and lacks a T cell autoepitope". Vaccine, 2002, 20: 2816-2825.
30. Olive C, Hsien K, Horvath A, Clair T, Yarwood P, Toth I, Good M F.: Protection against group A streptococcal infection by vaccination with self-adjuvanting lipid core M protein peptides. Vaccine, 2005 23(17-18):2298-303.
31. Pruksakorn S, Currie B, Brandt E R, Martin. D, Galbraith A, Phornphutkul C H, Hunsakunachai S, Manmontri A, Good M F: "Towards a vaccine for rheumatic fever: Identification of a conserved target epitope on M protein of group A streptococci". The Lancet, 1994; 344:639-642.
32. Raizada, V., Williams, R. C. Jr., Chopra, P., Gopinath, N., Prakash, K. et al: "Tissue distribution of lymphocytes in rheumatic heart valves as defined by monoclonal anti-T cells antibodies". Am. J. Med., 1983, 74, 90-96.
33. Robinson, J. H., Atherton, M. C., Goodacre, J. Á., Pinkney, M., Weightman, H. and Kehoe, M. A. (1991): "Mapping T-cell epitopes in group A streptococcal type 5 M protein". Infect. Immun. 59, 4324-4.
34. Scott, J R.; Hollingshead S K.; Fischetti V A: "Homologous regions within M protein genes in group A streptococci of differents serotypes". Infect. Immun. 1986, 52: 609-613.
35. Scott, J R.; Pulliam, W N.; Hollingshead S K.: "Fischetti V A. Relationship of M protein genes in group A streptococci". *Proc. Natl. Acad. Sci. USA.* 1985, 82: 1822-1827.
36. Snitcowsky, R.: "Rheumatic fever prevention in industrializing countries: problems and approaches". Pediatrics. 1996, 97(6): 996-998.
37. Vohra H, Dey N, Gupta S, Sharma A K, Kumar R, McMillan D, Good M F.: M protein conserved region antibodies opsonise multiple strains of *Streptococcus pyogenes* with sequence variations in C-repeats. Res Microbiol., 2005, 156(4):575-82.
38. WHO, I V R: New vaccines against infectious diseases: research and development status, April, 2005, updated February 2006.

The invention claimed is:

1. An immunogenic composition against group A beta hemolytic streptococcus comprising an isolated polypeptide, wherein (i) the only epitopes of *S. pyogenes* M protein contained within the polypeptide are the T and B epitopes, and (ii) the polypeptide has an amino acid sequence comprising the amino acid sequence set forth in SEQ ID NO: